United States Patent

Satoh et al.

[11] Patent Number: 5,264,421
[45] Date of Patent: Nov. 23, 1993

[54] FOOD COMPOSITION

[75] Inventors: Toshio Satoh; Hitoshi Matsumoto; Yasunori Niiro; Hisao Kakegawa, all of Tokushima; Tokutaro Miki, Hachioji, all of Japan

[73] Assignee: Nippon Hypox Laboratories, Incorporated, Tokyo, Japan

[21] Appl. No.: 852,167

[22] PCT Filed: Jul. 18, 1991

[86] PCT No.: PCT/JP91/00959
§ 371 Date: Apr. 6, 1992
§ 102(e) Date: Apr. 6, 1992

[87] PCT Pub. No.: WO92/01393
PCT Pub. Date: Feb. 6, 1992

[30] Foreign Application Priority Data

Jul. 18, 1990 [JP] Japan ................... 2-189810

[51] Int. Cl.$^5$ .................. A61K 31/70; A61K 35/78; A23B 7/10
[52] U.S. Cl. .................... 514/25; 424/195.1; 426/52; 426/655; 435/139
[58] Field of Search ............ 426/52, 655; 514/25; 424/195.1; 435/139

[56] References Cited

U.S. PATENT DOCUMENTS 3,364,034 1/1968 Hoersch et al. ............. 99/98
4,056,637 11/1977 Hagiwara et al. ........... 426/52

FOREIGN PATENT DOCUMENTS

WO85/01421 4/1985 World Int. Prop. O.

OTHER PUBLICATIONS

O'Brien Nabors et al "Alternative Sweeteners" 1986 Marcel Dekker pp. 3, 311-313.
Furia Fenaroli's Handbook of Flavor Ingredients 1971, Chemical Rubber Cleveland pp. 152-153 "Licorice".
World Patents Index Latest Section Ch, Week 8723 Derwent Class D, AN 87-161144 and KR-B-8 602 155 (Yuhan) Dec., 1986 Abstract.
Patent Abstracts of Japan vol. 4, No. 73 (C-032) Nov. 1980.
Lewis, Medical Rotary, Wiley & Sons, NY, 1977, p. 275.

Primary Examiner—John W. Rollins
Attorney, Agent, or Firm—Nixon & Vanderhye

[57] ABSTRACT

A food composition prepared from a lactic acid fermented aqueous liquorice extract which is free of the disadvantages of extremely strong sweetness which makes liquorice extracts unsuitable for maintaining and enhancing the pharmacological activities (both disease preventing and treating effects) of treating ulcers and hepatic diseases.

6 Claims, 2 Drawing Sheets 5,264,421

FOOD COMPOSITION

TECHNICAL FIELD

The present invention relates to a food composition prepared from a lactic acid fermented aqueous liquorice extract.

TECHNICAL BACKGROUND

Liquorice described in the Japanese Pharmacopoeia (glycyrrhiza; National Formulary, Liquirtitiae Radix in the European Pharmacopoeia) long been used as a flavoring or medicinal. In particular, its main component, glycyrrhizin, is 150 times sweeter than sucrose, and liquorice is being widely used as a sweetener even today.

On the other hand, liquorice extract is known to have pharmacological effects such as an antiulceration effect (Takagi, K., Ishii, Y., Arzein Forsch. 17, 1544 (1967)) and a protection effect against hepatopathy.

Since liquorice extract contains a relatively large amount of glycyrrhizin, its sweetness is very high. For this reason, the use of liquorice as a food composition is limited. As a result, it has been very difficult to take full advantage of health and therapeutic effects of liquorice extract.

An object of the present invention is to provide health food and therapeutic compositions containing liquorice extract.

DISCLOSURE OF THE INVENTION

The present inventors have found that a specific treatment of a liquorice extract makes it possible to take full advantage of the health and therapeutic effects inherent to the liquorice extract and provides palatable food compositions containing this extract.

PREFERRED EMBODIMENTS OF THE INVENTION

Figure 1:
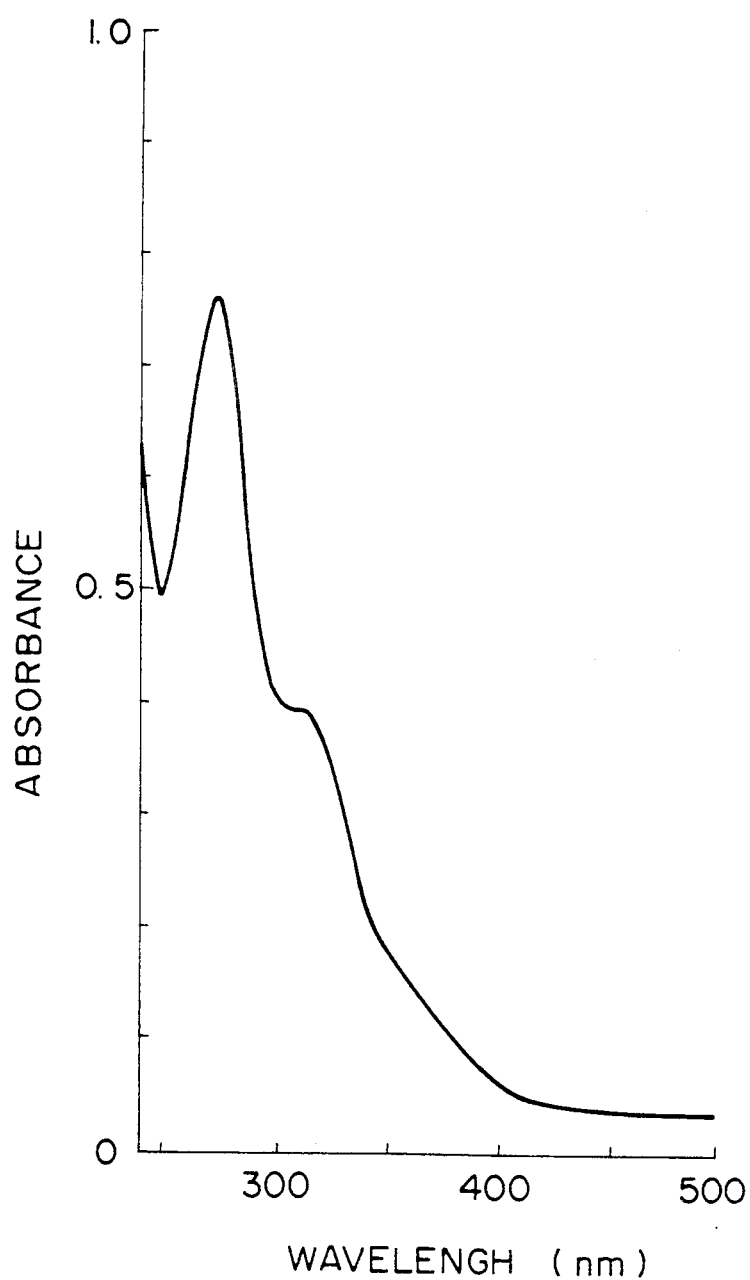
FIG. 1 shows the absorption spectrum of one embodiment of a composition of the present invention for a food product in visible and ultraviolet regions.

Food compositions of the present invention contain an extract obtained from a plant of the liquorice genus (Glycyrrhiza genus) used as a raw material. An aqueous liquorice extract solution (an aqueous solution obtained by extracting a liquorice with water) is particularly preferred. The "liquorice" refers to liquorice conventionally used as a sweetener, an excipient, a drug of Chinese medicine, etc. Examples thereof include the following plants.

Manchurian liquorice
  (*Glycyrrhiza uralenis* Fisch. et DC)
Koka liquorice
  (*G. glabra* Linne)
Spanish liquorice
  (*G. glabra* L var. *typica* Reg. et Herd)
Russian liquorice
  (*G. glabra* L var. *Glandulifera* Reg. et Herd)
Persian liquorice
  (*G. glabra* L var. *violacea* Boiss.)

The aqueous liquorice extract solution of any one of these liquorice plants is obtained by adding to water liquorice in an amount of 1 to 1,000 times the amount of the liquorice (w/w), and subjecting the mixture to heat treatment at 5° to 140° C. for 0.1 to 72 hours. When the liquorice extract aqueous solution is prepared, raw liquorice may be used as it is, while the use of dry liquorice is particularly preferred. When raw liquorice or dry liquorice is used, the whole plant or partial plant (root, stolon, etc.) thereof may be used, while a dry root from which the skin is removed and a dry stolon from which the skin is removed are particularly preferred. A liquorice is used preferably in a powder form. One may also use a solution prepared by dissolving a conventional liquorice extract used in Chinese medicine in water 1 to 1,000 times (w/w) the amount of the liquorice extract or a solution prepared by suspending a crude liquorice extract in water 1 to 1,000 times (w/w) the amount of the crude liquorice extract. The aqueous liquorice extract solution of the present invention also includes these solutions.

Food compositions of the present invention are produced by the lactic acid fermentation of an extract obtained from a plant of the liquorice genus (Glycyrrhiza genus) as described above. When the above liquorice extract aqueous solution is used as an extract, the composition of the present invention for a food comprises a fermentation liquid obtained by lactic acid fermentation of the liquorice extract aqueous solution (the fermentation liquid is sometimes referred to as "composition I for a food" hereinafter). Further, the composition of the present invention may comprise a semisolid or solid substance obtained by removing water from the above fermentation liquid (this substance is sometimes referred to as "composition II for a food" hereinafter).

As bacteria for the fermentation of the above liquorice extract aqueous solution, there may be used lactic acid bacteria which are conventionally used to obtain dairy products. Particularly preferred are lactic acid bacteria of the lactobacillus genus and lactic acid bacteria of the bifidobacterium genus. Lactic acid bacteria of these genera may be used alone or in combination. Further, lactic acid bacteria contained in a dairy product such as yogurt may be used together with the dairy product.

The lactic acid fermentation of the liquorice extract aqueous solution can be carried out by mixing the liquorice extract aqueous solution with lactic acid bacteria or a dairy product containing lactic acid bacteria and allowing the mixture to stand in a facultative anaerobic state for 1 day to 1 year. The mixture may optionally contain an agar medium, etc., as a nutrient source for the lactic acid bacteria. When lactic acid bacteria contained in a dairy product is used together with the dairy product, no other nutrient source is necessary since the dairy product series as a nutrient source for the lactic acid bacteria.

It is preferred to carry out the lactic acid fermentation such that isoliquiritin (a component derived from liquorice), lactic acid (a metabolite of lactic acid bacteria) and glycyrrhizin (a component derived from liquorice) are formed in the following proportions in the fermentation liquid; the amount of lactic acid based on 1 part by weight of isoliquiritin is 16 to 500 parts by weight, and the amount of glycyrrhizin based on 1 part of isoliquiritin is $\frac{1}{3}$ to 30 parts by weight. The isoliquiritin and glycyrrhizin contained in the liquorice extract aqueous solution decrease in amounts as the lactic acid fermentation of the liquorice extract aqueous solution continues. The amount of lactic acid in the fermentation liquid generally increases with an increase in the period of time for the fermentation.

When the amount of lactic acid based on 1 part by weight of isoliquiritin is less than 16 parts by weight, the amount of lactic acid relative to the amount of glycyrrhizin is small, and the fermentation liquid is therefore too sweet to eat or take. When the amount of lactic acid based on 1 part by weight of isoliquiritin exceeds 500 parts by weight, the amount of lactic acid relative to the amount of glycyrrhizin is large, and the fermentation liquid is too sour to eat or take. The amount of glycyrrhizin based on 1 part by weight of isoliquiritin is preferably not more than 14 parts by weight, particularly preferably not more than 10 parts by weight.

The composition I of the present invention for a food, obtained by the lactic acid fermentation of the liquorice extract aqueous solution as above, may comprise any one of the following fermentation liquids a to g.

a. A lactic acid fermentation liquid itself obtained above (sometime referred to as "fermentation liquid A" hereinafter).

b. A liquid prepared by subjecting the fermentation liquid A to a sterilization treatment generally carried out in the process of food production, particularly preferably to a sterilization treatment under heat (sometimes referred to as "fermentation liquid B" hereinafter).

c. A liquid prepared by removing insolubles contained in the fermentation liquid A by filtration or centrifugal separation (sometimes referred to as "fermentation liquid C" hereinafter).

d. A liquid prepared by removing insolubles contained in the fermentation liquid B by filtration or centrifugal separation sometimes referred to as "fermentation liquid D" hereinafter).

e. A liquid prepared by subjecting the fermentation liquid C to a sterilization treatment generally carried out in the process of food production, particularly preferably to a sterilization treatment under heat (sometimes referred to as "fermentation liquid E" hereinafter).

f. A liquid prepared by mixing at least two members elected from the group consisting of the fermentation liquid A, the fermentation liquid B, the fermentation liquid C, the fermentation liquid D and the fermentation liquid E (sometimes referred to as "fermentation liquid F" hereinafter).

g. A concentrate of any one of fermentation liquid A to the fermentation liquid F (to be sometime referred to as "fermentation liquid G" hereinafter).

In the present invention, these liquids are all referred to as fermentation liquids obtained by lactic acid fermentation of the aqueous liquorice extract solution.

Any one of the above fermentation liquids A to G contains, based on 1 part by weight of isoliquiritin, 16 to 500 parts by weight of lactic acid and ⅓ to 30 parts by weight of glycyrrhizin. Further, all of these fermentation liquids show absorption in the ultraviolet region of approximately 265 to 275 nm and in the region of approximately 305 to 320 nm. And, a 5 w/v % aqueous solution of any one of these fermentation liquids forms a white precipitate when methanol, ethanol or acetone is added.

Meanwhile, as described earlier, composition II of the present invention for a food includes a semisolid or solid substance obtained by removing water from the fermentation liquid (the above composition I for a functional food) obtained by lactic acid fermentation of the liquorice extract aqueous solution. Water contained in the composition I for a functional food can be removed by a conventional method such as a concentration treatment under reduced pressure or a freeze drying treatment.

The above composition II for a food product also contains, based on 1 part by weight of isoliquiritin, 16 to 500 parts by weight of lactic acid and ⅓ to 30 parts by weight of glycyrrhizin. Further, an aqueous solution of the composition II for a food product shows ultraviolet absorption in the region of approximately 265 to 275 nm and in the region of approximately 305 to 320 nm. And, a 5 w/v % aqueous solution of the composition II for a food product forms a white precipitate when methanol, ethanol or acetone is added.

In addition, composition I and composition II for a food, provided by the present invention, generally have the following biological characteristics.

Microorganism tests

*Escherichia coli*: negative
Yellow staphylococcus: negative
*Pseudomonas aeruginosa*: negative Both the so-obtained composition I and composition II for a food, provided by the present invention, have pharmacological activities such as protection activity against hepatopathy, antiulceration activity and inhibition activity against lipid hyperoxidation. And, these pharmacological activities are generally higher than those of a liquorice extract aqueous solution which has not subjected to lactic acid fermentation. The food compositions of the present invention retain their healthful and therapeutic effects. The food product composition of the present invention has appropriate sour taste and almost no persistent sweetness inherent to liquorice. Therefore, the composition of the present invention for a food that is fit to eat or take easily in view of its taste. It may also be incorporated into other food.

The food products of the present invention comprise a food containing the above composition of the present invention for a food. The food as a base is not specially limited, and food products include drinks such as water, a refreshing beverage and fruit juice, confectionery, breads, noodles, seasonings, etc.

The functional food of the present invention can be easily obtained by adding the composition of the present invention to a food as a base, or by adding the composition of the present invention after a food as base has been produced. A flavor may also be added.

Although differing depending upon the kinds of foods and likes and dislikes of people, the content of the above composition in the food product is preferably at least 0.1% by weight to obtain the health and therapeutic effects inherent in liquorice.

The present invention, will be explained hereinafter by reference to the following Examples.

EXAMPLE 1

Preparation of Food Composition I

20 Grams of an official liquorice powder (skin removed) was added to 1 liter of water, and the liquorice was subjected to extraction under heat at about 90° C. for 1 hour. After the resultant extract solution containing the liquorice powder was cooled, lactic acid bacteria contained in yogurt, Morinaga Bihidas (trade name, supplied by Morinaga Milk Industry Co., Ltd.) were added to the extract solution together with the yogurt. The mixture was recharged into a glass container, and the container was tightly closed and kept in a fucultative anaerobic state by turning the containiner upside down.

Thereafter, the container was allowed to stand at room temperature for 2 weeks for lactic acid fermentation except that the container as a whole was sometimes shaken.

After 2 weeks, the contents were taken out of the container and subjected to suction filtration, and the filtrate was sterilized at 90° C. for 90 minutes to give about 0.9 liter of a composition I of the present invention.

The above-obtained composition I was analyzed by high pressure liquid chromatograph under the following conditions to show that it was composed of at least 20 components.

Column: Cosmosil $_5C_{18}$ [trade name, supplied by Nakaraitisc K.K.].

Mobile phase: a liquid prepared by adjusting a mixture of methanol with water (methanol:water volume ratio=60:40) to pH of 2.1 with phosphoric acid.

Flow rate: 1.5 ml/minute

Detector: ultraviolet and visible light spectrophotometer (detection wavelength: 250 nm).

Table 1 shows the peak retention time and content of each component, found by the analysis by high pressure liquid chromatography under the above conditions.

Further, FIG. 1 shows the absorption spectrum of the above-obtained composition of a functional food in visible and ultraviolet regions.

COMPARATIVE EXAMPLE 1

Example 1 was repeated except that neither lactic acid bacteria contained in yogurt, Morinaga Bihidas (trade name, supplied by Morinaga Milk Industry Co., Ltd.), nor the yogurt was added to the extract, to give a composition (a liquorice extract).

The above-obtained composition was analyzed by high pressure liquid chromatography under the same conditions as those in Example 1 to show that the composition contained at least 22 components.

Table 2 shows the peak retention time and content of each component, found by the analysis by high pressure liquid chromatography.

TABLE 1

| Peak No. | Peak retention time (minute) | Content (%) (relative value) |
|---|---|---|
| 1 | 1.278 | 31.0454 |
| 2 | 1.488 | 47.032 |
| 3 | 2.013 | 3.3482 |
| 4 | 2.197 | 3.4418 |
| 5 | 2.44 | 1.5189 |
| 6 | 2.85 | 0.2678 |
| 7 | 3.273 | 1.6347 |
| 8 | 3.728 | 0.14 |
| 9 | 4.025 | 0.3368 |
| 10 | 4.333 | 0.9275 |
| 11 | 4.83 | 1.3007 |
| 12 | 5.167 | 0.1319 |
| 13 | 6.217 | 3.4368 |
| 14 | 6.825 | 0.6054 |
| 15 | 8.15 | 0.0385 |
| 16 | 12.207 | 0.1094 |
| 17 | 13.578 | 1.4096 |
| 18 | 14.593 | 0.1158 |
| 19 | 20.997 | 3.0003 |
| 20 | 22.627 | 0.1584 |

TABLE 1-continued

| Peak No. | Peak retention time (minute) | Content (%) (relative value) |
|---|---|---|
| | Total: | 100 |

TABLE 2

| Peak No. | Peak retention time (minute) | Content (%) (relative value) |
|---|---|---|
| 1 | 1.3 | 12.6402 |
| 2 | 1.5 | 24.0965 |
| 3 | 1.72 | 8.5805 |
| 4 | 2.008 | 5.7122 |
| 5 | 2.448 | 2.5415 |
| 6 | 2.863 | 0.9072 |
| 7 | 3.282 | 1.9451 |
| 8 | 3.75 | 0.5617 |
| 9 | 4.02 | 0.7241 |
| 10 | 4.328 | 1.2734 |
| 11 | 4.843 | 2.6625 |
| 12 | 6.05 | 4.8634 |
| 13 | 6.867 | 0.9857 |
| 14 | 7.977 | 0.0314 |
| 15 | 8.228 | 0.093 |
| 16 | 10.608 | 0.031 |
| 17 | 13.647 | 3.6049 |
| 18 | 14.607 | 0.324 |
| 19 | 19.117 | 0.2161 |
| 20 | 21.077 | 24.9749 |
| 21 | 22.747 | 3.0003 |
| 22 | 25.298 | 0.2304 |
| | Total: | 100 |

A comparison of data shown in Tables 1 and 2 clearly shows the following. In the food composition I of the present invention, obtained in Example 1, the content (relative value) of glycyrrhizin decreased to 1/5 or less (a component indicated by peak No. 19 in Table 1 and a component indicated by peak No. 20 in Table 2), while the components found within a peak retention of 2 minutes increased.

EXAMPLE 2-EXAMPLE 4

Preparation of Food Composition I

Compositions of the present invention were prepared in the following manner. At first, 30 g each of official liquorice powders was suspended in 1 liter of distilled water, and subjected to extraction under heat at about 70° C. for 2 hours. After the resultant extract solutions containing the liquorice powder were cooled to room temperature, lactic acid bacteria contained in 200 g of yogurt, Morinaga Bihidas (trade name, supplied by Morinaga Milk Industry Co., Ltd.) were aseptically added to each extract solution together with the yogurt. The mixtures were recharged into glass containers, and the glass containers were tightly closed and kept in a fucultative anaerobic state by turning the container upside down.

Then, the glass containers were allowed to stand at 30° to 35° C. for 3 days for lactic acid fermentation except that each glass container as a whole was sometimes shaken.

After 3 days, the contents (lactic acid fermentation solution) in each glass container were boiled to terminate the fermentation, then allowed to cool to room temperature, and centrifugally separated. After the centrifugation, the supernatants were recovered to give about 0.8 liter each of compositions I of the present invention for a food.

Table 3 shows the contents of the compositions for a food, obtained in these Examples. For a comparison, Table 3 also shows the contents of the liquorice extract solution obtained by suspending 30 g of an official liquorice powder in 1 liter of distilled water and subjecting the mixture to extraction under heat at about 70° C. for 2 hours.

TABLE 3

|  | Example 2 | Example 3 | Exaple 4 | Liquorice extract solution |
|---|---|---|---|---|
| Isoliquiritin (μg/ml) | 45 | 38 | 17 | 160 |
| Lactic acid*1 (μg/ml) | 4,200 (93.3) | 2,600 (68.4) | 1,500 (88.2) | 5 or less (0.03 or less) |
| Glycyrrhizin*1 (μg/ml) | 63 (1.4) | 52 (1.4) | 160 (9.4) | 2.298 (14.4) |
| Liquiritin (μg/ml) | 240 | 840 | 580 | 1,280 |
| Glycyrrhetic acid (μg/ml) | not detected | not detected | not detected | not detected |
| Isoliquiritigenin (μg/ml) | nbot detected*2 | not detected*2 | not detected*2 | 4.2 |
| pH | 3.8 | 3.8 | 4.0 | 5.6 |

*1: Parenthesized values show amounts based on 1 part by weight of isoliquiritin
*2: Detection limit: 1 μg/ml.

Figure 2:
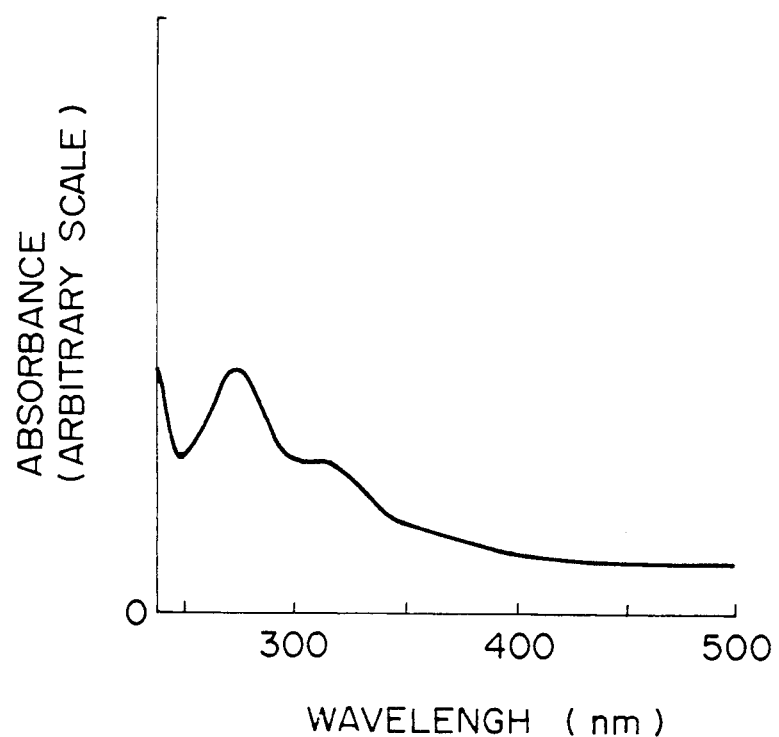
FIG. 2 shows the absorption spectrum of other embodiment of the composition of the present invention for a functional food in visible and ultraviolet regions.

As is shown in Table 3, the food compositions food contained 16 to 500 parts by weight, based on 1 part by weight of isoliquiritin, of lactic acid, and ⅓ to 30 parts by weight, based on 1 part by weight of isoliquiritin, of glycyrrhizin. In contrast, such a liquorice extract solution as the liquorice extract solution for a comparison generally shows no lactic acid, or the content of lactic acid is very small as shown in FIG. 2.

Further, when the above compositions I for a food were tasted by five male adults, every adult reported that the compositions I, obtained in Examples 2 and 3, were not sweet, and four out of the five adults reported that the composition, obtained in Example 4, was not sweet.

The compositions I were respectively diluted 25-fold with water, and each solution was measured for an absorption spectrum in the visible and ultraviolet regions in the same manner as in Example 1 to show an ultraviolet absorption in the regions of approximately 265 to 275 nm and 305 to 320 nm. FIG. 2 shows the absorption spectrum of the composition I, obtained in Example 2, in the visible and ultraviolet regions.

Further, when 5 w/v % aqueous solutions of the above compositions I were prepared and 5-fold methanol was added to these solutions, a white precipitate was formed in each of the solutions. A white precipitate was also formed when the methanol was replaced with ethanol and when the methanol was replaced with acetone.

EXAMPLE 5

Preparation of Food Composition I

40 Grams of an official liquorice powder (skin removed) and 5 g of an agar medium were added to 1 liter of water, and the liquorice was subjected to extraction under heat at 70° C. for 2 hours. After the extract solution containing the liquorice powder and the agar medium was cooled, *Lactobacillus bulgaricus* as lactic acid bacteria was added to the extract solution, and the mixture was treated in the same manner as in Example 1 to give about 0.9 liter of a composition I of the present invention.

EXAMPLE 6

Preparation of Food Composition I

20 Grams of an official liquorice powder (skin removed) and 5 g of yogurt [trade name, Meiji Bulgaria Yogurt, supplied by Meiji Milk Products Co., Ltd.] were added to 1 liter of water, and the liquorice was subjected to extraction under heat at 70° C. for 2 hours. After the extract solution containing the liquorice powder and the yogurt was cooled, *Bifidobacterium longum* as the lactic acid bacteria was added to the extract solution, and the mixture was treated in the same manner as in Example 1 to give about 0.9 liter of a composition I of the present invention for a food.

EXAMPLE 7

Preparation of Food Composition I

100 Grams of a dried product of the whole of Spanish liquorice was cut to thin pieces, and these pieces were added to 1 liter of water. Then, the Spanish liquorice was subjected to extraction under heat at 70° C. for 2 hours. After the extract solution containing the thin pieces of the Spanish liquorice was cooled, *Lactobacillus casei* as the lactic acid bacteria was added to the extract solution, and the mixture was treated in the same manner as in Example 1 to give about 0.9 liter of a composition I of the present invention for a functional food.

EXAMPLE 8–EXAMPLE 10

Preparation of Food Composition II

The food compositions I, obtained in Examples 2 to 4 were respectively freeze-dried to give 9.5 to 15.8 g of solids (compositions II).

Aqueous solutions of these food compositions II were prepared, and each solution was measured for an absorption spectrum in the visible and ultraviolet regions to show ultraviolet absorption in the regions of approximately 265 to 275 nm and 305 to 320 nm.

Further, when 5 w/v % aqueous solutions of the above-prepared compositions II were prepared and 5-fold methanol was added to each of these solutions, a white precipitate was formed in each solution. A white precipitate was also formed when the methanol was replaced with ethanol and when the methanol was replaced with acetone.

EXAMPLE 11

Preparation of Food Composition

The composition I, obtained in Example 7, was concentrated under reduced pressure to give 20 g of a soft extract food (composition II).

An aqueous solution of the above soft extract was prepared, and was measured for an absorption spectrum in the visible and ultraviolet regions to show ultraviolet absorption in the regions of approximately 265 to 275 nm and 305 to 320 nm.

A 5 w/v % aqueous solution of the above soft extract was prepared, and 5-fold methanol was added to the aqueous solution to form a white precipitate. A white precipitate was also formed when the methanol was replaced with ethanol and when the methanol was replaced with acetone.

PHARMACOLOGICAL TEST 1

Activity on Carbon Tetrachloride Hepatopathy

The liver production activity of the composition I of the present invention was assayed in the following manner in accordance with an assay using model mice having acute hepatopathy induced by carbon tetrachloride [Toxicol. Appl. Pharmacol., 67, 159 (1983)] which has been established for assaying the liver protection activity.

At first, twenty-three male ICR mice weighing about 30 g were prepared, and divided into five groups consisting of 4 or 5 mice.

Then, one (4 mice) out of the five groups was used as a control of group, and each individual mouse of this control group was hypodermically administered on its back a mixture containing an olive oil and carbon tetrachloride in an olive oil:carbon tetrachloride volume ratio of 10:1 in a dose of 0.1 ml per 10 g of the mice weight to cause acute hepatitis. Then, immediately after the administration, 12 hours after the administration, and 48 hours after the administration, a physiological saline solution was orally administered in a dose of 0.5 ml/mice. Then, 48 hours after the third administration of the physiological saline solution, the mice were sacrificed, and their bloods were collected and measured for a GOT (glutamic-oxaloacetic transaminase) amount and a GPT (glutamic-pyruvic transaminase) amount in the serum by a conventional method.

The remaining four groups were divided to a group of mice which were to be administered with the composition I, obtained in Example 1 (Example group 1, 5 mice), a group of mice which were to be administered with the composition I, obtained in Example 5 (Example group 2, 4 mice), a group of mice which were to be administered with the composition I, obtained in Example 6 (Example group 3, 5 mice), and a group of mice which were to be administered with the composition (liquorice extract aqueous solution) obtained in Comparative Example 1 (Comparative Example group 1, 5 mice). And, in the same manner as in the case of the control group, the mice of these groups were caused to have acute hepatitis. They were orally administered with one of the compositions I, obtained in the Examples, or the composition obtained in Comparative Example 1, in place of the physiological saline solution. Then, the procedures in the case of the control group were repeated to measure a GOT amount and GPT amount in the serum from each group.

Table 4 shows the results.

TABLE 4

| Group | N | GOT amount*1 | GPT amount*1 |
|---|---|---|---|
| Control group | 4 | 5,895 ± 1348 | 11,089 ± 1,818 |
| Example group 1 | 5 | 2,097 ± 1,960*2 | 4,967 ± 2,793*3 |
| Example group 2 | 4 | 2,661 ± 2,018*2 | 5,218 ± 3,664*2 |
| Example group 3 | 5 | 2,493 ± 1,620*2 | 4,219 ± 2,062*2 |
| Comparative Example group 1 | 5 | 3,980 ± 1,670*2 | 7,120 ± 1,720*3 |

*1: unit = unit/liter
*2: Significant difference at a significance level of 5 % in t-assay of students.
*3: significant difference at a significance level of 1 % in t-assay of students.

As is clearly shown in Table 4, the GOT amount and GPT amount of each of the Example groups 1 to 3 which were administered in one of Examples 1, 5 and 6, are significantly smaller than those of the control group, and these GOT amount and GPT amount are also smaller than those of the Comparative Example group 1 which were administered with the liquorice extract aqueous solution.

The above results show that the liver protection activity of the composition I provided by the present invention, is higher than the liver protection activity of a liquorice extract aqueous solution.

It has been already clear that part of the toxicity of carbon tetrachloride to the liver is derived from a lipid peroxidation reaction by $CCl_3$ radical which is generated in a living body. Therefore, the composition I for a functional food, provided by the present invention, has been tested in the following Pharmacological Test 2 to see whether it inhibits the lipid peroxidation reaction induced by $CCl_4$.

PHARMACOLOGICAL TEST 2

Anti-oxidation Activity Against Lipid Peroxidation Reaction

Specimen solutions, i.e., the composition I, obtained in Example 2, a mixture of a liquorice extract aqueous solution obtained in the same manner as in Example 2 with yogurt (to be sometimes referred to as "0 day-fermentation solution" hereinafter) and an alcohol solution of isoliquiritin, were tested on anti-oxidation activity in the following manner.

Rat liver microsomes were obtained by a conventional method, and suspended in 1.15% KCl to obtain a microsome suspension containing 2 mg/ml of proteins.

Then, 100 μl of the above microsome suspension, 200 μl of an NADPH-forming aqueous solution (containing 30 mM of G-6-P, 5 IU/ml of G-6-P dehydrogenase, 3.2 mM of NADP and 80 mM of nicotinamide) and 100 μl of one of the specimen solutions which were adjusted to a concentration as shown in Table 5 with a 10% DMF aqueous solution were added to 500 μl of a tris-HCl buffer, and the resultant mixture was warmed at 37° C. for 5 minutes.

Then, 100 μl of carbon tetrachloride (100 mM 10 v/v % DMSO solution) was added, the mixture was warmed at 37° C. for 20 minutes, and the reaction was terminated by cooling the mixture with ice. Thereafter, the 1 ml of the reaction solution was taken and measured for an amount of formed lipid peroxide by a thiobarbituric acid method. The antioxidation activities of the specimen solutions were compared with the result of a blank solution, and expressed as an inhibition ratio (%).

In addition, in the blank solution, the specimen solution was replaced with 100 μl of 10% DMF, the 200 μl of the NADPH-forming aqueous solution was replaced with 100 μl of water, and 100 μl of the carbon tetrachloride (100 mM 10 v/v % DMSO solution) was replaced with 100 μl of a 10 v/v % DMSO solution.

Table 5 shows the results

TABLE 5

|  | Concentration | Lipid peroxidation inhibition ratio (%) |
|---|---|---|
| Composition I for functional food | 10 μl/ml | 11 |
|  | 20 μl/ml | 26 |
|  | 100 μl/ml | 86 |
| 0-day fermentation solution | 10 μl/ml | 0 |
|  | 100 μl/ml | 59 |

As is clear from Table 5, when the specimen solutions had the same concentration, the lipid peroxidation inhibition ratio in a group which had been administered with the composition I for a functional food was higher than the lipid peroxidation inhibition ratio in a group which had been administered with the 0-day fermentation solution.

The above results show that the composition I, provided by the present invention, has higher antioxidation activity than the 0-day fermentation solution. It is also understood from these results that the composition I, provided by the present invention, has liver protection activity as shown in the above Pharmacological Test 1. It is further understood that at least part of the above liver protection activity is based on the antioxidation activity of the composition I, provided by the present invention.

PHARMACOLOGICAL TEST 3

Antiulceration Activity

The composition I for a functional food, obtained in Example 2, and a mixture of a liquorice extracted aqueous solution obtained in the same manner as in Example 2 with yogurt (to be sometimes referred to as "0 day-fermentation solution" hereinafter) were tested on the antiulceration activity against hydrochloric acid-ethanol ulcer in the following manner.

Male SD rats weighing 180 to 220 g (5 rats/group) were fasted for 24 hours, and then a 60% ethanol solution containing 150 ml of hydrochloric acid (hydrochloric acid-ethanol solution) was orally administered to individual rats in a dose of 0.5 ml per 100 g of the weight to cause hydrochloric acid-ethanol ulcer.

One hour after the administration of the hydrochloric acid-ethanol solution, and each rat was etherized and sacrificed by bleeding. Their stomachs were extirpated, and after each stomach was fixed, the ulcer which occurred in the glandular portion of each stomach was measured for a length. The total length of the ulcer of each rate was calculated and taken as an ulcer coefficient.

In addition, the composition I and the 0-day fermentation solution had been respectively concentrated under reduced pressure to ¼ of the starting volume and used as a specimen solution. These specimen solutions had been orally administered to the rats in a dose of 1 ml per 100 g of the rat weight 30 minutes before the administration of the hydrochloric acid-ethanol solution. For the control group, the specimen solution had been replaced with distilled water in the same amount as that of the specimen solution.

Table 6 shows the results.

TABLE 6

|  | Number of rats (N) | Ulcer coefficient (average value ± standard error) |
|---|---|---|
| Control | 5 | 191.2 ± 16.9 |
| Composition I for functional food | 5 | 22.8 ± 3.2 |
| 0-day fermentation solution | 5 | 109.0 ± 17.7 |

Table 6 clearly shows that the ulcer coefficient of the group which has been administered with the composition I is smaller than the ulcer coefficient of the group which has been administered with the 0-day fermentation solution.

It is understood from the above results that the composition I, provided by the present invention, has higher antiulceration activity than the 0-day fermentation solution.

PHARMACOLOGICAL TEST 4

90 Days' Subacute Toxicity Test and 30 Days' Recovery Test

Male Wistar rats aged 5 weeks were orally administered with the composition I of the present invention, obtained in Example 1, in a dose of 10 ml/rate continuously for 90 days. Then, the recovery test was carried out for 30 days.

As a result, no change was observed in parameters such as the general condition, the weight, the chemical inspection of the blood, electrolytes in the urine during the administration period and recovery period.

The above result clear show that the composition I for a functional food, provided by the present invention, has no toxicity.

PANEL TEST

The food composition I of the present invention, obtained in Example 1, was 10-fold diluted with water, and the mixture was cooled to about 4° C. and used as a test liquid. The test liquid was tasted by 10 male panelists having an age of 22 to 55, 40 ml each, before lunch, and their evaluations were collected.

The panelists' evaluations were as follows, provided that a plurality of evaluations were accepted.

| | |
|---|---|
| 1. Tasted suitably sour and tasted good. | 6 |
| 2. Tasted sour bitterly and tasted foreign. | 0 |
| 3. Dull feeling in the legs and arms disappeared and fresh feling occurred. | 3 |
| 4. Refreshing feeling remained in the mouth and an appetite was increased. | 4 |
| 5. Flatulent feling temporarily occurred in the abdomen, but an appetite was soon increased. | 1 |
| 6. Tasted sweet. | 0 |
| 7. Smelled foreign. | 0 |

Out of the ten panelists, two panelists having a hangover reported that the sick feeling and the languor caused by the hangover had disappeared.

EXAMPLE 12

Preparation of Functional Food

The composition 1 for a functional food, obtained in Example 1, was used as one of raw materials to prepare 1,000 cc of a soft drink (one of the functional foods of the present invention) having the following composition.

| Orange juice | 17.5 g |
|---|---|
| Grape fruit juice | 14.0 g |
| Pineapple juice | 4.2 g |
| Fruit sugar, grape sugar, liquid sugar (BX:75) | 140 g |
| Citric acid | 4.0 g |
| Flavor | 1.0 g |
| Composition I | 5.0 g |
| Purified water | remainder |

EXAMPLE 13

Preparation of Food

The composition 1, obtained in Example 2, was used as one of raw materials to prepare a refreshing drink (one of the foods of the present invention) having the following composition.

| Purified water | 38.70 g |
|---|---|
| Composition I for a functional food | 58.03 g |
| Sugar | 2.90 g |
| Sodium citrate | 0.07 g |
| L-ascorbic acid | 0.10 g |
| Sodium chloride | 0.05 g |
| Citric acid | 0.1 g |
| Taste adjuster | proper amount |
| Flavor | proper amount |

EXAMPLE 14

Preparation of Food

The composition 1, obtained in Example 5, was used as one of raw materials to prepare 1,000 cc of a carbonated drink (one of the foods of the present invention) having the following composition.

| Granulated sugar | 4.2 g |
|---|---|
| Citric acid | 1.0 g |
| Vitamin C | 0.1 g |
| Grape skin color | 5.0 g |
| Flavor | 1.8 g |
| Composition I | 5.0 g |
| Carbonated water | remainder |

EXAMPLE 15

Preparation of Food

The composition 1, obtained in Example 6, was used as one of raw materials to prepare 200 g of caramel (one of the foods of the present invention) having the following composition.

| Sugar | 70.0 g |
|---|---|
| Glutinous starch syrup | 83.0 g |
| Condensed milk | 30.0 g |
| Flour | 9.38 g |
| Milk | 18.75 g |
| Butter | 2.25 g |
| Coconut oil | 0.75 g |
| Composition I | 5.0 g |

EXAMPLE 16

Preparation of Food

Example 11 was repeated to obtain 20 g of a composition II (soft extract), and the composition II was used as one of raw materials to prepare 300 g of cookie (one of the foods of the present invention) in the following manner.

20 Grams of the soft extract (the composition II for a food), 100 g of sugar and 80 g of butter were mixed and kneaded. Then, an egg yolk, 200 g of flour and a proper amount of a vanilla essence were added, and the mixture was kneaded.

The above-obtained mixture was allowed to stand at 4° C. for 1 hour, and then baked to cookies according to a general cookie preparation method, whereby 300 g of cookies containing the food composition II were obtained.

EXAMPLE 17

Preparation of Food

The composition I, obtained in Example 1, was used as one of raw materials. This composition I was added to raw materials for wheat noodles so that the content of the composition I in the noodles was 1% by weight. Then, the mixture was treated according to a general noodle-cooking method to obtain noodles (one of the foods of the present invention).

The food products obtained in Examples 12 to 17 were respectively tasted by five male adults, and they reported that all of these foods tasted good to eat.

As specified above, the food composition, provided by the present invention, has higher pharmacological activities such as liver protection activity, antiulceration activity and lipid peroxidation inhibition activity than an aqueous liquorice extract solution which has not been subjected to lactic acid fermentation. Further, the food composition, provided by the present invention, is not only fit to eat or take as it is, but it is also fit to eat or take as the food product of the present invention.

Therefore, according to the present invention, the health maintenance effect and therapeutic effect inherent to liquorice can be easily and fully utilized.

We claim:

1. A food composition which comprises a fermentation solution obtained from the lactic acid fermentation of an aqueous liquorice extract, which contains, per part by weight of isoliquiritin, 16 to 500 parts by weight of lactic acid and $\frac{1}{3}$ to 30 parts by weight of glycyrrhizin, and which fermentation solution exhibits the following properties:

(1) has absorption peaks in the ultraviolet ranges approximately of 265 to 275 nm and 305 to 320 nm, and
   (2) precipitates a white product when methanol, ethanol or acetone is added to a 5 w/v % aqueous solution thereof.

2. A food composition which comprises a semi-solid or solid substance obtained from the lactic acid fermentation of an aqueous liquorice extract solution and the subsequent removal of water from the resultant fermentation solution, which semi-solid or solid substance contains, per part by weight of isoliquiritin, 16 to 500 parts by weight of lactic acid and $\frac{1}{3}$ to 30 parts by weight of glycyrrhizin, and which semi-solid or solid substance exhibits the following properties:

(1) an aqueous solution thereof has absorption peaks in the ultraviolet ranges approximately of 265 to 275 nm and 305 to 320 nm, and
   (2) forms a white precipitate product when methanol, ethanol or acetone is added to a 5 w/v % aqueous solution thereof.

3. The food composition according to claim 1 or 2, wherein the fermentation solution contains, per part by weight of isoliquiritin, 16 to 500 by weight of lactic acid and ⅛ to 14 parts by weight of glycyrrhizin.

4. The food composition according to claim 1 or 2, wherein the fermentation solution contains, per part by weight or isoliquiritin, 16 to 500 by weight of lactic acid and ⅛ to 10 parts by weight of glycyrrhizin.

5. The food composition according to claim 1 or 2, wherein the fermentation solution is obtained by subjecting the aqueous liquorice extract to lactic acid fermentation in a facultative anaerobic state at 1° to 40° C. for 1 day to 1 year.

6. An aqueous beverage, aqueous solution, fruit juice, confectionery, bread, noodle or seasoning containing the food composition of claim 1 or 2 therein.

* * * * *